United States Patent [19]

Martin

[11] 3,976,457

[45] Aug. 24, 1976

[54] IN-STACK FILTER CELL

[75] Inventor: Robert M. Martin, Durham, N.C.

[73] Assignee: The United States of America as represented by the Administrator of the United States Environmental Protection Agency, Washington, D.C.

[22] Filed: Aug. 13, 1975

[21] Appl. No.: 604,397

[52] U.S. Cl. .................................. 55/270; 55/502; 55/504; 55/527; 73/421.5 R
[51] Int. Cl.² ...................................... B01D 53/30
[58] Field of Search ............. 55/270, 478, 480, 486, 55/487, 501, 504, 502, 511, 527; 73/421.5 R, 421.5 A, 28

[56] References Cited
UNITED STATES PATENTS

| | | | |
|---|---|---|---|
| 2,909,415 | 10/1959 | Houdry | 55/DIG. 30 |
| 3,417,549 | 12/1968 | Leosis | 55/522 |
| 3,528,279 | 9/1970 | Lasseur et al. | 55/270 |
| 3,693,410 | 9/1972 | Robrecht et al. | 55/511 |
| 3,748,905 | 7/1973 | Fletcher et al. | 73/28 |
| 3,841,145 | 10/1974 | Boubel | 55/270 |
| 3,932,153 | 1/1976 | Byrns | 40/455 |

*Primary Examiner*—Bernard Nozick

[57] ABSTRACT

A new filter cell which has particular utility in an isokinetic in-stack particulate collection system can be inserted directly into standard three-inch or four-inch portholes which are prevalent in the stacks which are to be tested. The filter cell is attached to a probe, both of which are inserted into the stack so that a fluid containing the particulate enters the filter cell parallel to a fiber filter which is contained therein. The fluid passes downward through the filter fiber and then exits the filter cell parallel to the fiber filter through an outlet port, leaving the particulate matter trapped in the filter.

4 Claims, 2 Drawing Figures

IN-STACK FILTER CELL

FIELD OF THE INVENTION

This invention essentially relates to a filter cell which meets the standards of the Environmental Protection Agency (EPA) and which may be used in an EPA reference method train for determining the amount of pollutants contained in an industrial stack or duct.

BACKGROUND OF THE INVENTION

In 1967, the Abatement Branch of the National Center for Air Pollution Control formed a group to undertake stack sampling. At that time, there was no standard system of stack sampling equipment which was directly applicable to the needs of the Branch. Thereafter, a system was designed to determine the amount of particulates or pollutants which are contained in an industrial stack. This system is used as the standard system as referenced in the Federal Register, Vol. 35, No. 247, Dec. 23, 1971, and is known as Method 5. Essentially, all Federally accepted data in support of New Source Performance Standards for particulate matter, and for determining compliance with particulate standards, is based upon this system. Commercially available equipment conforming to this EPA design is widely obtainable and is used for collecting the desired data. However, the sample box containing the fiber filter in this system contains much elaborate and delicate glass equipment thereby complicating the testing of the particulate matter. Furthermore, this sample box cannot be inserted through the standard three-inch or four-inch portholes which are contained in a great number of the stacks.

Many other methods and apparatus for measuring particulate emissions in a gas flow have been developed. One such apparatus is shown in U.S. Pat. No. 3,841,145 to Boubel. This apparatus, which comprises a stack sampler for collecting particulate samples in gaseous emissions, would appear at first glance to be quite similar to the present invention; however, there are very major and important differences. The Boubel device is a high-volume sampling system involving a number of components which together are used for extracting a large sample volume from a stack. This device is designed specifically to obtain a large sample of particulate matter in a short period of time, but is limited to those sources with emissions which are low in temperature and moisture content. While this device has merit for use on such sources, it is not equivalent to, and cannot satisfy the requirements which are essential in the EPA Standards.

Furthermore, since the Boubel device is a high-volume sampling system, the filter area which must be employed is of such a large size as to prohibit its insertion in the three- and four-inch standard ports, and therefore it must be used as an out of stack sampler. Additionally, the data collected from this Boubel out-of-stack filter cell, which cannot be subjected to high temperature emissions, would be different than that collected in an in-stack filter cell since the physical state of the emissions can be different in both filter cells.

SUMMARY OF THE INVENTION

It is accordingly an object of the present invention to overcome the defects of the prior art as stated above.

Another object of the present invention is to provide for improved sampling of stack particulates.

Another object of the present invention is to provide a filter cell which may be used in the EPA reference train.

A further object of the present invention is to provide a filter cell which may be used in high moisture situations.

Yet another object of the present invention is to produce a filter cell which can be inserted in standard three-inch or four-inch ports.

A further object of the above invention is to provide a filter cell which is easy to clean and easy to replace the filter.

Still another object of the above invention is to provide a filter cell which has a high temperature range.

These and other objects of the invention are fulfilled by utilizing a filter cell having a substantially rectangular glass fiber filter having the approximate dimensions of 2 × 6 or 2 × 7. Therefore, the size of the filter area is equivalent to that of the standard three-inch circular filter which is used in the EPA reference system, but which now can be inserted into a typical 3-inch or 4-inch port contrary to the prior art circular filter.

The filter cell itself is composed of a substantially cylindrical housing having an inlet port communicating with the interior of the cell housing for drawing a flow of gas into the filter cell housing. A preweighed filter is disposed in this housing substantially parallel to the flow of the gas. After the gas flows through the filter and the particulate is trapped in the filter, it exits the cell housing via an outlet port placed under the filter. After a predetermined period of time, the filter cell is removed from the stack, disassembled, and the filter itself is weighted to determine the amount of pollutants in the stack. This filter cell is to be used in conjunction with the EPA reference train and, therefore, the measuring instruments which are used in that train measure the isokinetic gas flow and other variables.

The present device can be used in stacks which contain high moisture content, such as those on scrubbers, wet processes, or combustion processes. Additionally, the present filter cell is operated in the stack such that the temperature of the filter media is maintained at the temperature of the gas stream.

BRIEF DESCRIPTION OF THE DRAWING

The above and additional objects and advantages of the present invention will become more apparent by reference to the description of illustrated embodiments in a drawing thereof in which.

DETAILED DESCRIPTION OF A PREFERRED EMBODIMENT

Figure 1:
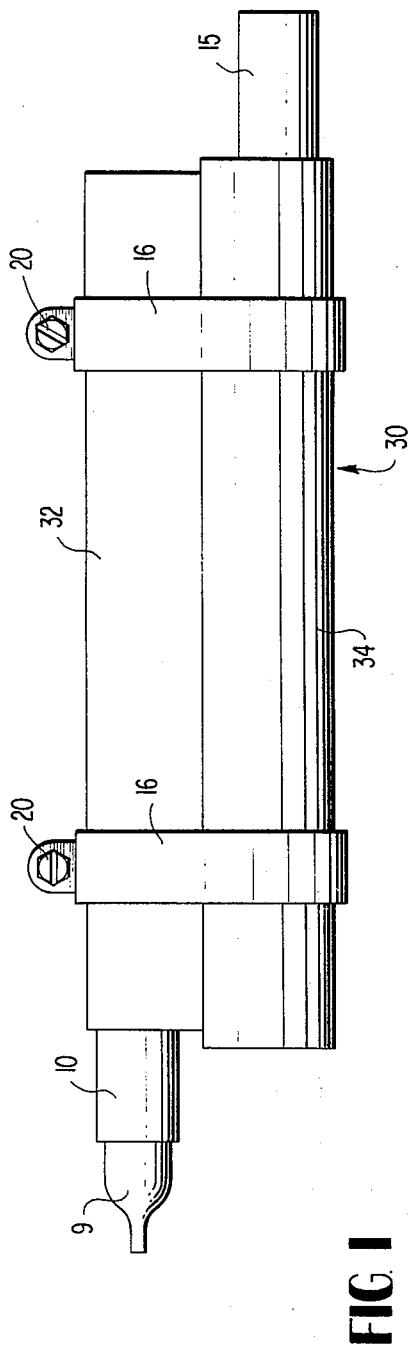
FIG. 1 is a side view of the filter cell in accordance with the invention.

FIG. 1 shows a filter cell 30 which is to be placed directly into a stack or duct to test the level of pollutants therein. This cell, preferably tubular in shape, consists of a top semi-cylindrical housing 32 and a bottom semi-cylindrical housing 34 which can essentially be a longitudinally cut stainless steel tube, although the exact constructional material is not crucial. An inlet port 10 which is connected to a nozzle 9 is in communication with the interior of the cell 30 so that the gaseous flow through the stack will be directed into the cell 30. A pair of hose clamps 16 which are tightened by screws 20 encircle the cell 30 to insure a tight, leakless seal. An outlet port 15 is connected to the bottom housing tube 34 and allows the gas to exit from the cell 30. This outlet port 15 is also attached to a probe in the EPA reference train which is in communication with a testing console to insure the isokinetic flow of the gas and to measure other variables.

Figure 2:
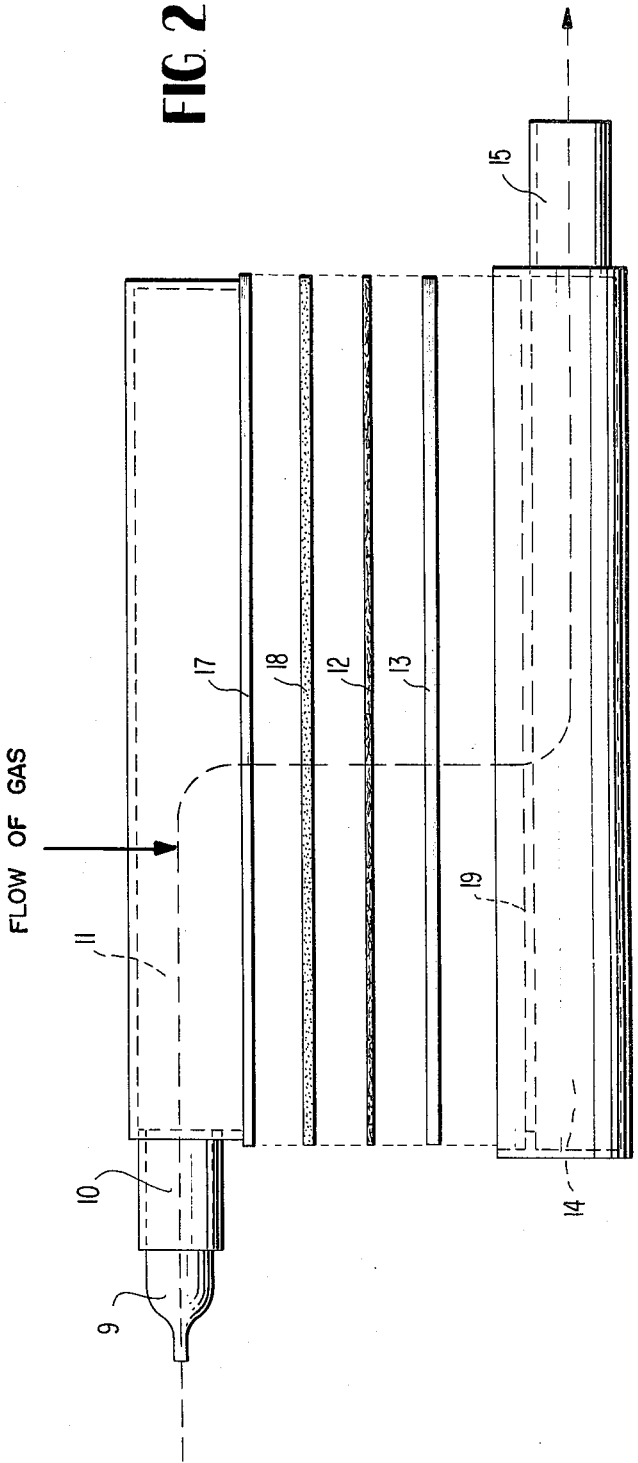
FIG. 2 is an exploded view of the filter cell showing its several components.

FIG. 2 shows the interior of the filter cell and discloses the several components contained therein. As can be seen from the Figure, a substantially rectangular filter 12 is provided which is aligned parallel to the flow of gas (dashed line in FIG. 2) as it enters a top chamber 11 in the top housing 32 from the nozzle 9 and the inlet port 10. The disposition of the inlet and outlet ports in relation to the filter 12 to obtain gas flow parallel to the filter 12 is an important feature of the device. This filter 12 must be preweighed before it is inserted into the cell 30 to insure accurate measurement of the pollutants. The filter 12 should be constituted of a glass fiber material and must have the same total area as the circular fiber filters utilized in the EPA Standard reference train. This is accomplished by using a rectangular shaped filter having dimensions between 1 by 3 inches and 1 by 4 inches.

A perforated or sintered stainless steel rectangular plate 13 is included to support the filter 12 and allow the gas to flow into a bottom chamber 14 in the bottom housing 34 and out of port 15 to an acceptable metering device. To insure stability, the filter 12 and the filter support 13 are supported by a filter support rest 19 which is disposed in the bottom chamber 14.

A gasket 18 encircles the cell 30 to insure a leakless seal and can be constructed of Teflon, silicone rubber, or any like substance for low temperature applications, or it can be constructed of asbestos such as that used for automobiles for use at elevated temperatures. If silicone rubber is used, the gasket should be provided with a central web that insures gasket seals on the edges. To also insure that a minimum amount of leakage occurs, the inlet port 10 and the outlet port 15 are connected to the nozzle 9 and probe, respectively, with standard Swagelok fittings or the like. Additionally, during sampling, the filter cell 30 may protrude out of the stack slightly and, if this occurs, the filter cell should be insulated by covering it with suitable insulating material, e.g. cloth such as asbestos cloth.

The filter cell 30 is assembled and closed securely by use of the two hose clamps 16 which, upon tightening, force a flange 17 down onto the gasket 18 providing a leakless seal.

The above-described device operates in the following manner: before the filter cell 30 is assembled, the glass fiber filter 12 is weighed and then mounted on filter support 13 and the filter support rest 19 in the bottom chamber 14. The entire cell 30 is then placed directly within a stack and a sample of gas from this emission source is isokinetically drawn to the device in which particulate matter is collected on the filter. The filter cell 30 is then removed from the emission source, disassembled, and the filter 12 is then weighed and calculations may be made which quantify the amount of emissions from the source.

While this device has been described in great detail, it can be appreciated by those who possess ordinary skill in the art that certain modifications may be made to this device without deviating from the scope of this invention. Therefore, this invention is not to be construed to be limited to what is shown in the drawings and described in the specification.

What is claimed is:

1. A filter cell sampling device for collecting particulate matter directly within a stack or duct during an isokinetic flow of gas containing the particulate matter through the stack or duct, comprising:

a generally tubular closed housing of two generally hemi-cylindrical separable halves for direct insertion into the stack or duct and having an elongated inlet chamber and an elongated outlet chamber, the inlet and outlet chambers both extending substantially the axial length of the cylindrical housing;

inlet means for drawing the flow of gas into said housing, said inlet means including an inlet nozzle at the upstream end of and communicating with the inlet chamber of said housing in one end thereof;

a preweighed filter means in sheet form in said housing extending substantially the length thereof and disposed downstream of the inlet chamber parallel to and lying between the elongated inlet and outlet chambers and parallel to the flow of gas entering said housing from said inlet at the end of the inlet chamber, said filter being disposed upstream from the outlet chamber and being formed of a heat and moisture resistant material, and means in said housing to support and to hold said filter in sheet form;

sealing means between the halves of said housing for ensuring a leakless seal; and outlet means for directing the flow of gas out of said housing, said outlet means being disposed downstream of the outlet chamber in the end of the housing generally opposite the location of said inlet means to direct the flow of gas through the outlet chamber generally parallel to said filter means.

2. A filter cell according to claim 1 wherein said preweighed filter means is constructed of a glass fiber and has a rectangular configuration measuring approximately 2 by 6 inches.

3. A filter cell according to claim 1 wherein said housing is insertable into standard 3 or 4 inch portholes.

4. A filter cell according to claim 1 further including a perforated plate below said filter means for supporting said filter means.

* * * * *